(12) United States Patent
Hansen et al.

(10) Patent No.: US 6,516,802 B2
(45) Date of Patent: Feb. 11, 2003

(54) METHOD AND COMBINATION FOR TREATING SLEEP APNEA USING A CANTILEVER MASK ATTACHMENT DEVICE

(75) Inventors: Gary L. Hansen, Eden Prairie, MN (US); Steven S. Bordewick, Shoreview, MN (US); Nicole Denise Bloom, San Francisco, CA (US)

(73) Assignee: Mallinckrodt, Inc., St. Louis, MO (US)

( * ) Notice: Subject to any disclaimer, the term of this patent is extended or adjusted under 35 U.S.C. 154(b) by 0 days.

(21) Appl. No.: 09/846,256

(22) Filed: May 2, 2001

(65) Prior Publication Data

US 2001/0015204 A1 Aug. 23, 2001

Related U.S. Application Data

(63) Continuation of application No. 09/436,406, filed on Nov. 9, 1999, now Pat. No. 6,347,631, which is a continuation-in-part of application No. 09/276,799, filed on Mar. 26, 1999.

(51) Int. Cl.[7] ............................................. A62B 18/08
(52) U.S. Cl. ............................ 128/207.11; 128/207.13
(58) Field of Search ..................... 128/207.11, 207.13, 128/207.17, 207.18

(56) References Cited

U.S. PATENT DOCUMENTS

| | | | | |
|---|---|---|---|---|
| 1,081,745 A | * | 12/1913 | Johnston et al. | ........ 128/207.13 |
| 1,282,527 A | * | 10/1918 | Bidonde | ................ 128/207.18 |
| 1,287,149 A | * | 12/1918 | Walter et al. | |
| 3,040,741 A | * | 6/1962 | Carolan | ................ 128/207.11 |
| 3,752,157 A | * | 8/1973 | Malmin | ................ 128/207.11 |
| 3,850,168 A | * | 11/1974 | Ferguson et al. | ...... 128/206.27 |
| 4,080,664 A | * | 3/1978 | Morris et al. | .......... 128/207.11 |
| 4,373,523 A | * | 2/1983 | Treutelaar | ............. 128/207.18 |
| H397 H | | 1/1988 | Stark | |
| 4,782,832 A | | 11/1988 | Trimble et al. | |
| 5,243,971 A | * | 9/1993 | Sullivan et al. | ........ 128/207.13 |

(List continued on next page.)

FOREIGN PATENT DOCUMENTS

| | | | | |
|---|---|---|---|---|
| DE | 186290 | * | 6/1907 | ............ 128/207.11 |
| DE | 659476 | * | 5/1938 | ............ 128/206.27 |
| EP | 0549299 | | 6/1993 | |
| FR | 385538 | * | 3/1908 | ............ 128/207.11 |
| FR | 2517545 | | 10/1983 | |
| WO | 9804310 | | 2/1998 | |
| WO | 9848878 | | 5/1998 | |
| WO | 9824499 | | 6/1998 | |

OTHER PUBLICATIONS

Updated "Skalpi" advertisement, www.skymall.com.

Primary Examiner—Aaron J. Lewis
(74) Attorney, Agent, or Firm—Rothwell, Figg, Ernst & Manbeck, p.c.

(57) ABSTRACT

A continuous positive airway pressure (CPAP) system in combination with a device for positioning a breathing apparatus over a breathing orifice in the head of a person, the person having an occipital lobe and an axis of symmetry, the device including an occipital anchor for anchoring against the head of the person beneath the occipital lobe of the person. The device further including a forward anchor for anchoring against a forward portion of the person's head. A spring connector connects the forward anchor and the occipital anchor, and biases the occipital anchor against the head of the person beneath the occipital lobe and the forward anchor against the corresponding portion of the person's head so as to attach the device to the person's head. The occipital anchor, the forward anchor and the spring connector are substantially aligned along the axis of symmetry of the person's head. The mount is connected to the spring connector for mounting the apparatus so as to locate the apparatus over the orifice.

14 Claims, 4 Drawing Sheets

U.S. PATENT DOCUMENTS

| | | | |
|---|---|---|---|
| 5,421,799 A | | 6/1995 | Rabin et al. |
| D368,141 S | | 3/1996 | Rabin et al. |
| 5,611,771 A | | 3/1997 | Taylor |
| 5,657,752 A | * | 8/1997 | Landis et al. .......... 128/207.13 |
| 5,662,101 A | * | 9/1997 | Ogden et al. .......... 128/205.25 |
| D385,960 S | * | 11/1997 | Rudolph ................. D24/110.4 |
| 5,763,030 A | | 6/1998 | Matsui |
| 5,767,634 A | | 6/1998 | Taylor et al. |
| D405,538 S | | 2/1999 | Chih |
| 6,044,844 A | * | 4/2000 | Kwok et al. ........... 128/206.27 |
| 6,112,746 A | * | 9/2000 | Kwok et al. ........... 128/207.13 |
| 6,119,693 A | * | 9/2000 | Kwok et al. ........... 128/207.11 |
| 6,119,694 A | * | 9/2000 | Correa et al. .......... 128/207.18 |
| 6,192,886 B1 | * | 2/2001 | Rudolph ................ 128/207.17 |
| 6,247,470 B1 | * | 6/2001 | Ketchedjian ........... 128/207.17 |
| 6,347,631 B1 | * | 2/2002 | Hansen et al. ......... 128/207.11 |
| 6,357,441 B1 | * | 3/2002 | Kwok et al. ........... 128/207.13 |

* cited by examiner

METHOD AND COMBINATION FOR TREATING SLEEP APNEA USING A CANTILEVER MASK ATTACHMENT DEVICE

CROSS REFERENCE TO RELATED APPLICATIONS

This application is a continuation of U.S. Application Ser. No. 09/436,406 filed Nov. 9, 1999 (now U.S. Pat. No. 6,347,631), which is a continuation-in-part of U.S. Application Ser. No. 09/276,799 filed Mar. 26, 1999, the disclosures of which are incorporated herein by reference in their entirety.

BACKGROUND OF THE INVENTION

1. Field of the Invention

The present invention relates to the field of devices and methods for holding breathing devices and the like in place on a person's head.

2. Description of the Background Art

Breathing devices, such as masks and the like, typically are held in place on a person's face by a harness including one or more straps extending around the person's head and along the side of the person's face.

Known devices have a variety of drawbacks. If the strap system is complex, it may not be obvious to the prospective wearer how to properly use the system, and elderly patients may struggle with putting on a mask when help is not present.

A strap system which is incorrectly adjusted may result in improper positioning of the mask or excessive pressure to the skin.

Also, straps may contact sensitive regions of the face, resulting in abrasions or contact dermatitis over time.

Additionally, straps may obscure portions of the face, causing distress to the wearer from a personal and aesthetic point of view. This can contribute to lack of compliance with wearing of the mask.

There remains a need in the art for improved methods and devices for positioning breathing devices and the like on a person's head.

SUMMARY OF THE INVENTION

In accordance with the present invention, a device is provided for positioning a breathing apparatus in communication with (i.e., over or within) a breathing orifice in the head of a person, the head of the person having an occipital lobe and an axis of symmetry. The device comprises an occipital anchor structure for anchoring against the head of the person about (i.e., beneath or against) the occipital lobe of the person, a forward anchor member for anchoring against a corresponding portion of the person's head at a forward anchoring position selected from the group consisting of a first portion of the persons head proximally surrounding said orifice (such as an area surrounding the nose and/or mouth, including the bridge of the nose) and a region located from the top portion of the person's head to the forehead portion of the person's head, and a biasing structure (such as a spring, array of springs, or other biasing member) connecting the forward anchor and the occipital anchor. The biasing structure biases the occipital anchor against the head of the person beneath the occipital lobe and biases the forward anchor against the corresponding portion of the person's head so as to attach the device to the person's head. The occipital anchor, the forward anchor and the biasing structure are substantially aligned along the axis of symmetry of the person's head. A mounting member also is connected to the biasing structure for mounting said apparatus so as to locate the apparatus over said orifice.

DETAILED DESCRIPTION OF THE INVENTION

The present invention provides a novel device and method for positioning an apparatus over a portion of a person's head. The invention generally is for positioning a head orifice-interacting apparatus over an orifice of the person's head.

The present invention is particularly applicable to devices to control sleep apnea, or to assist in breathing.

In preferred embodiments, the invention is for positioning a breathing device such as a breathing mask or respirator mask for covering at least one facial member selected from the group consisting of a person's nose, a person's mouth and a combination thereof. However, the invention can also be applied for positioning an apparatus over a person's ear or ears, such as a listening apparatus; or for positioning an apparatus over a person's eye or eyes such as a viewing apparatus. Additionally, the device can be utilized for positioning a speaking apparatus over a person's mouth, or any combination of the above.

In the embodiments shown in FIGS. 1–6, the device of the invention is provided for attaching a breathing mask over a person's nose, mouth or both.

Figure 1:
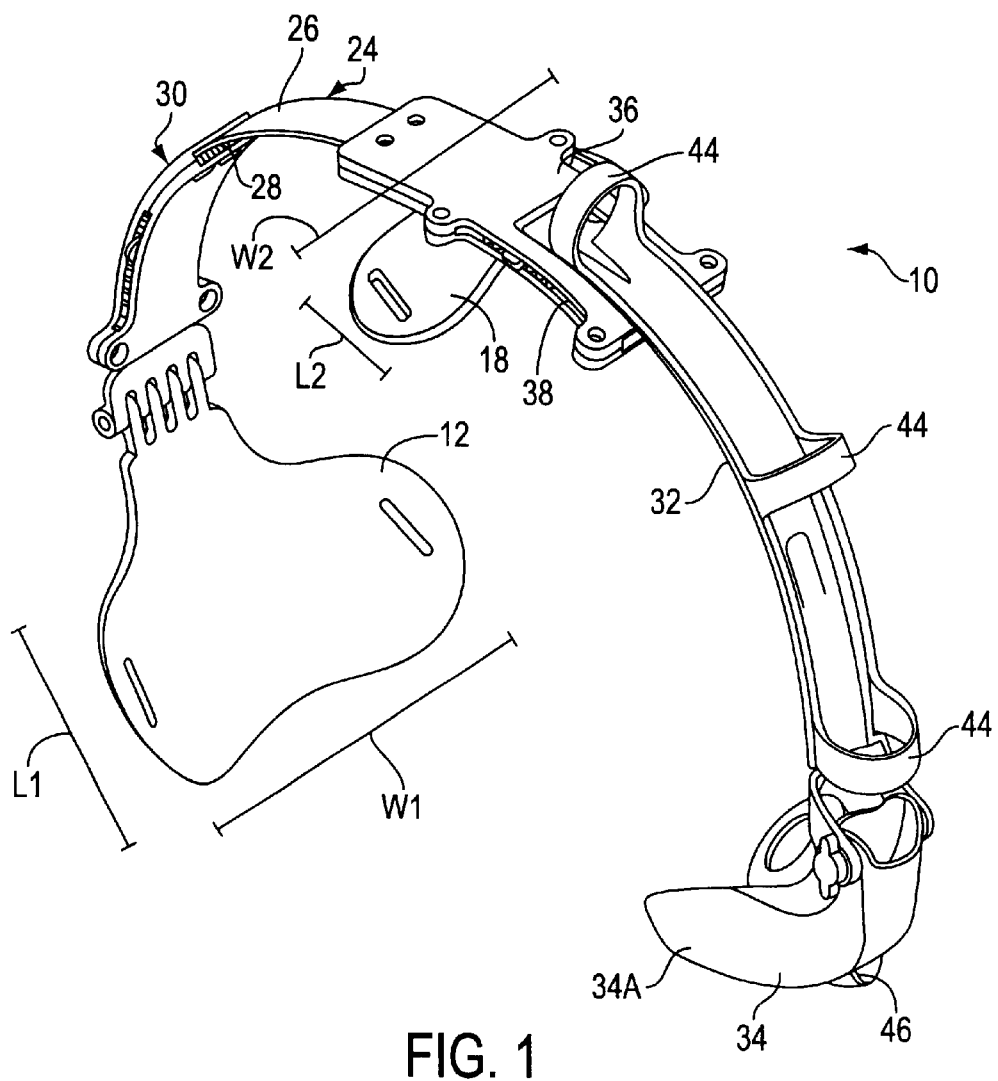
FIG. 1 is a perspective view of a device in accordance with one embodiment of the invention.
Figure 3:
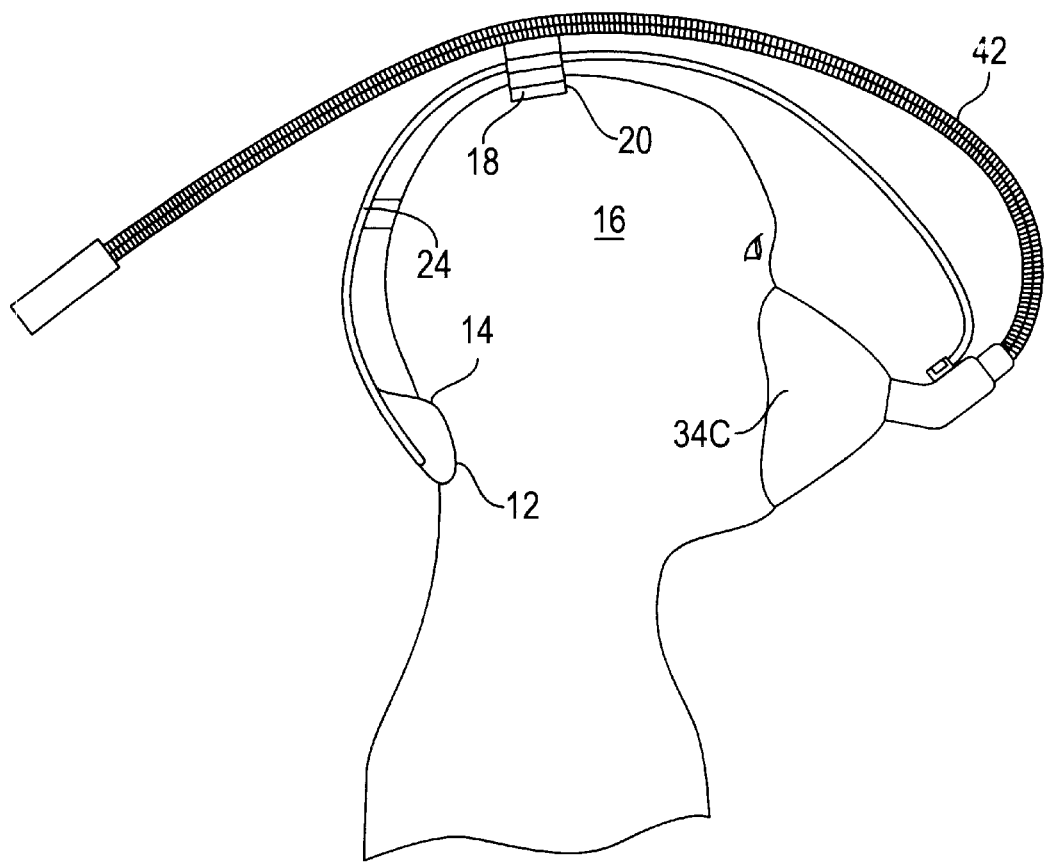
FIG. 3 is a side elevation view of a device in accordance with another embodiment of the invention.
Figure 4:
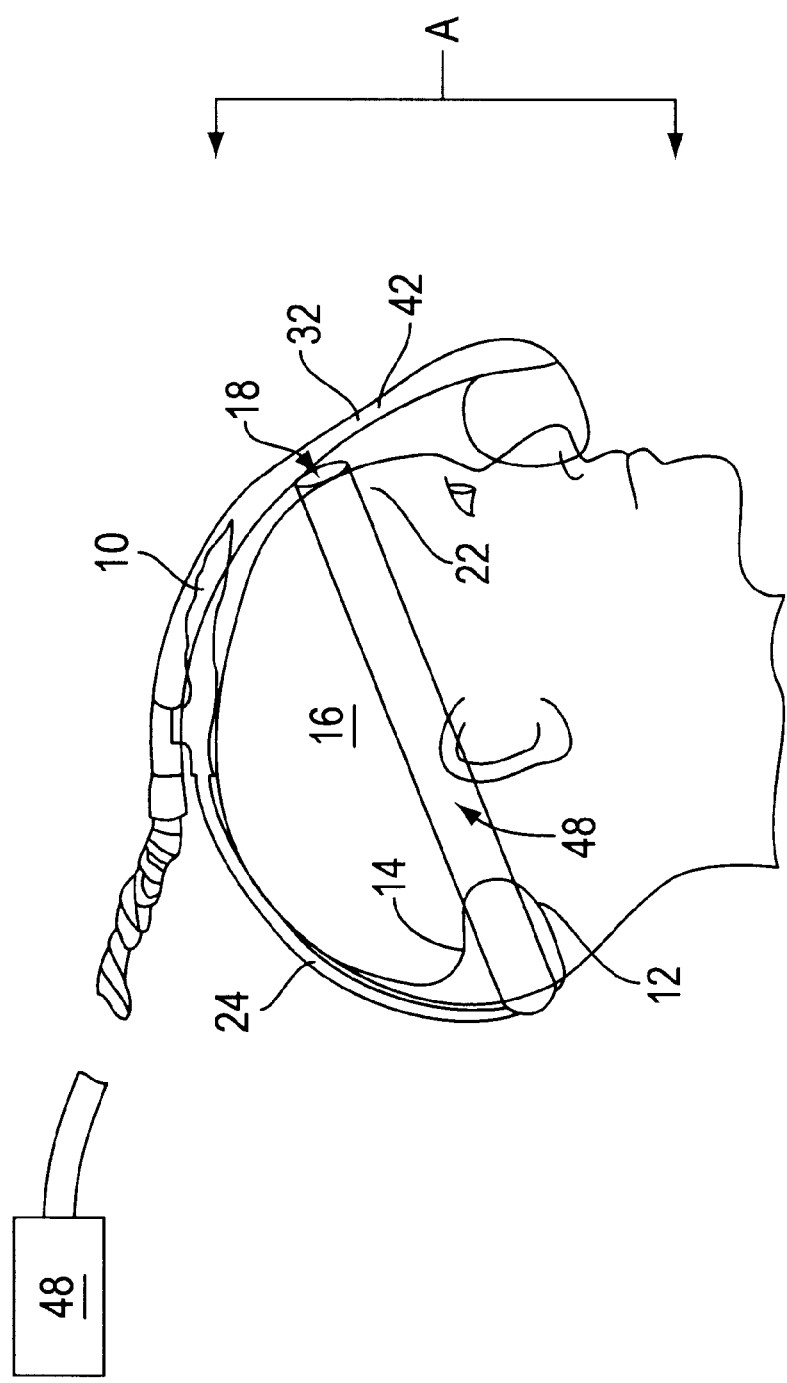
FIG. 4 is a schematic side elevational view of still another embodiment of the invention.

In the embodiment shown in FIG. 1, a device 10 in accordance with the present invention includes an occipital anchor 12 for anchoring against the inian portion of the person's head beneath the occipital lobe 14 of a person's head 16 shown in FIGS. 3 and 4. The occipital anchor 12 can have a length L1 within a range of about 2–8 centimeters, preferably about 3–7 centimeters, and a width W1 within a range of about 5 to 20 centimeters, preferably about 8–12 centimeters.

Referring back to FIG. 1, the device 10 includes a forward anchor member 18 for anchoring against a corresponding portion of the person's head selected from the group consisting of a top portion of the person's head 20 shown in FIG. 3, and a forehead portion 22 of a person's head shown in FIG. 4. As shown in FIG. 1, the forward anchor 18 can have a length L2 within a range of about 1 to 4 centimeters, preferably about 2 to 3 centimeters, and a width W2 within a range of about 5 to 11 centimeters, preferably about 7 to 9 centimeters.

The device 10 includes a biasing structure 24 connecting the forward anchor member 18 and the occipital anchor 12.

The biasing structure 24 biases the occipital anchor against the occipital lobe and the forward anchor against the top portion or the forehead portion of the person's head, so as to attach the device to the person's head.

The occipital anchor 12, the forward anchor 18 and the biasing structure 24 are substantially aligned along the axis A of symmetry of the person's head, which is in line with the plane of FIG. 4.

The biasing structure 24 extends between the occipital anchor 12 and the forward anchor 18 a distance within the range of about 7–30 centimeters, preferably about 10–18 centimeters. The biasing structure 24 can be formed of spring steel, and as shown in FIG. 1, the distance between the occipital anchor 12 and the forward anchor 18 can be adjusted by spring 26 sliding within slot 28 of scabbard member 30.

Referring to FIG. 1, a mounting member 32 is connected to the biasing structure 24 for mounting a breathing mask 34, which in this case is a nostril mask 34A, to sealingly engage the nostril mask with a person's nostrils.

The mounting member 32 can extend between the forward anchor 18 and the breathing mask 34 a distance within the range of about 10 to 25 centimeters, preferably about 15 to 20 centimeters. As shown in FIG. 1, the device 10 has a second scabbard member 36 with a slot 38 within which the spring member 26 is slidable for adjustment of the device.

Figure 2:
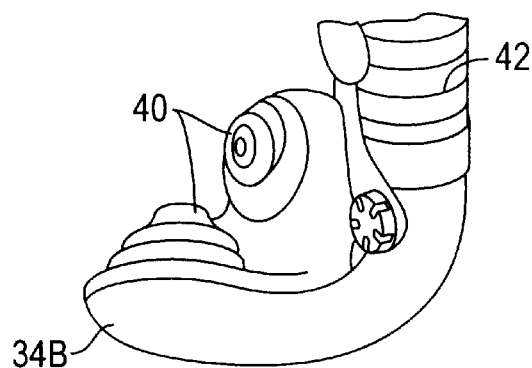
FIG. 2 shows details of a mask for use with the present invention including a pair of nostril-tubes for sealingly fitting within corresponding nostrils of a person's nose.

FIG. 2 shows a breathing mask 34B which is a Nasal Pillows™ type including a pair of nostril-tubes 40 for sealingly fitting within corresponding nostrils of a person's nose.

FIG. 3 shows a breathing mask 34C which sealingly covers both the patient's nose and mouth, the mounting member 32 being capable of biasing the breathing mask 34C so as to form a seal around the nose and mouth orifices.

In the embodiments shown, a gas plenum 42 is provided, as shown in FIGS. 2, 3 and 4. The embodiment shown in FIG. 1 shows structure for attaching a gas plenum to mounting member 32, including rings 44. The gas plenum is attached to the mounting member 32 and connectable to the breathing mask 34 for delivering gas to and from the breathing 30 mask 34. Alternatively, the gas plenum can be formed as an integral part of mounting member 32.

The plenum 42 can have any suitable cross-sectional area, for example, within a range of about 100 to 500 mm$^2$. In particularly preferred embodiments, the air plenum 42 is approximately 46 centimeters long and has a circular cross-section of 15 mm, with a cross-sectional area of about 175 mm$^2$.

In particularly preferred embodiments, the device 10 consists essentially of the occipital anchor 12, forward anchor 18, biasing structure 24 and mounting member 32, with the occipital anchor, forward anchor, biasing structure and mounting member being essentially the only means for attaching the breathing mask 34 to the person's head, the device being otherwise substantially free of any other means for securing the device to the person's head. In such embodiments, the device 10 is adapted to apply a force normal to the occipital anchor within a range of about 300–1,500 gm, with a preferred nominal force normal applied to the occipital anchor structure of about 800 gm. According to this embodiment, the preferred device is adapted to apply a force normal to the forward anchor 18 within a range of about 300 to 1,200 gm, with a nominal force normal applied to the forward anchor 18 of about 500 gm. The force normal applied to the breathing mask depends on whether the breathing mask is a Nasal Pillows™ (nostril-tube) type or a perimeter-type mask extending completely around the nose and mouth. For a Nasal Pillows™ type of mask, the goal is to minimize the force normal, whereas for a perimeter mask, a substantial force normal is required to make a sufficient air seal. Thus, a force normal applied to the breathing mask generally is within a range of about 0–1,000 gm, with a nominal force normal of about 100 gm being most preferred.

A device as shown in FIG. 1 preferably is adapted so that the lateral force necessary to cause side slippage on a person's head is within the range of about 200 to 500 mgm, with a nominal lateral force necessary to cause side slippage of greater than about 300 gm.

Additionally, with a device as shown in FIG. 1, there is a force downward at the nose due to air pressure and structural loading through the air plenum within a range of about 0–300 gm, nominally about 100 gm.

For increased security and/or to provide greater fixation of the device, a side strap 48 can be provided as shown in FIG. 4, passing around the sides of the head and connecting the occipital anchor 12 with the mounting member 32. Side strap 48 preferably is formed of cloth or elastomeric material.

Figure 5:
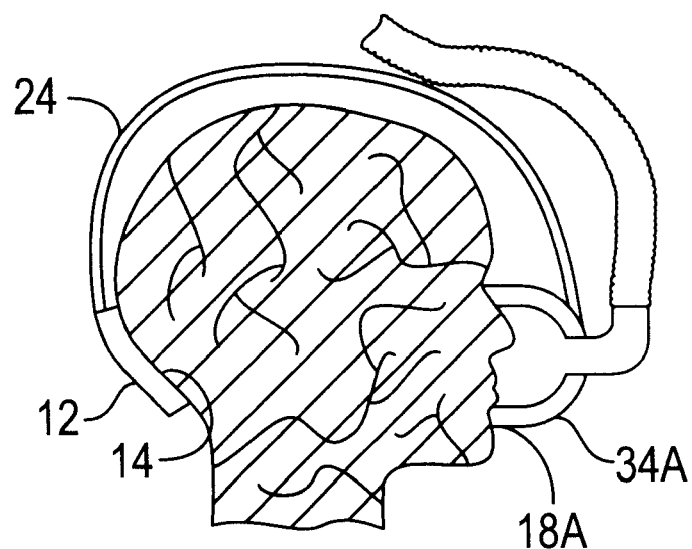
FIG. 5 is a schematic side elevational view of a further embodiment of the invention.
Figure 6:
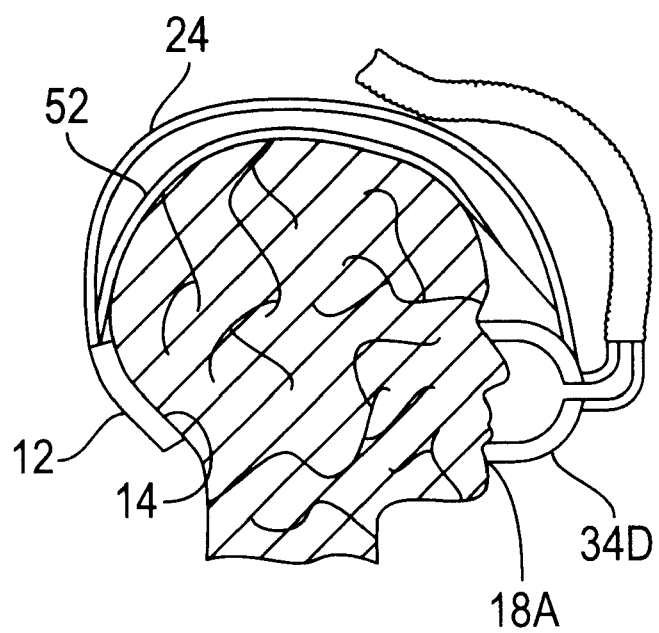
FIG. 6 is a schematic side elevational view of yet another embodiment of the invention.

FIGS. 5 and 6 show an embodiment where the forward anchor member 18A is comprised of the breathing apparatus such as mask 34D. In accordance with these embodiments, the spring force of biasing structure 24 holds the apparatus in place by pressure of face mask 34D against the front of the face and by pressure of occipital anchor 12 against the occipital lobe 14.

For increased security and/or to provide greater fixation of the device, a compliant sling 52 can be provided, having opposite ends connected to forward and rear portions of the biasing structure 24 as shown in FIG. 6. Sling 52 contacts the persons head when the breathing apparatus such as face mask 34D is located over the person's nose and/or mouth. Sling 52 provides frictional force at the top of the head, to aid in preventing the device from slipping sideways. The sling may be formed of any suitable compliant material such as fabric, plastic or the like, and may be elastic, inelastic or spring loaded. Sling 52 may also assist in rendering the device self-centering, wherein a perturbing lateral force is met by an opposing compensating force, so as to resist lateral slippage.

In the embodiment shown in FIG. 1, carbon dioxide-rich gas that the patient exhaled exits the system through vent 46 which is sized so that continuous positive airway pressure (CPAP) within the plenum flushes the hose and the plenum between breaths. A carbon dioxide vent is generally disclosed in U.S. Pat. No. 5,065,756, reissued as RE. 35,339, incorporated herein by reference.

The method of the present invention utilizing a device as shown in the figures includes the steps of positioning the occipital anchor against a person's occipital lobe, positioning the forward anchor against the corresponding portion of the person's head, and positioning the breathing mask over the person's nose, mouth or both, with the occipital anchor, the forward anchor and the biasing structure substantially aligned along the axis of symmetry of the person's head, and with the occipital anchor, forward anchor and breathing mask biased against the corresponding portions of the patient's head. When a CPAP system is utilized with the invention, the method of the invention includes the step of connecting the gas plenum 42 to a continuous source of respiratory gas 50, shown schematically in FIG. 4. In preferred embodiments, the method further includes the step of removing expired gas containing carbon dioxide from the gas plenum through vent 46 when the person exhales.

While many modifications, variations and changes in detail may be made to the described embodiments, it is intended that the matter in the foregoing description and shown in the accompanying drawings be interpreted as illustrative and not in a limiting sense.

What is claimed is:

1. A method of treating sleep apnea utilizing a breathing mask and a mask attachment device having an occipital anchor adapted to fit against the head of a person beneath their occipital lobe, a forward anchor adapted to fit against the person's head at a forward anchoring position selected from the group consisting of a first portion of the person's head proximally surrounding a breathing orifice and a region selected from the group consisting of a top portion of the person's head and a forehead portion of the person's head, a biasing structure extending from the occipital anchor to the forward anchor, and a mounting member extending from said forward anchor for mounting the breathing mask, said method comprising the steps of positioning the occipital anchor about the person's occipital lobe, and the forward anchor against the corresponding portion of the person's head, such that the breathing mask is in communication with at least one breathing orifice of the person and the occipital anchor, the forward anchor, and the biasing structure are substantially aligned along an axis of symmetry of the person's head, the biasing structure biasing the occipital anchor against the person's occipital lobe, the forward anchor against the corresponding portion of the person's head, and the breathing mask against the portion of the person's head proximally surrounding the breathing orifice;

connecting the mask to a continuous positive airway pressure (CPAP) system; and providing respirator gas from the CPAP system to the person via the mask to prevent apnea while the person sleeps.

2. The method of claim 1, wherein the positioning step includes positioning the forward anchor on a top portion of the person's head rearwardly of the person's forehead.

3. The method of claim 1, wherein the positioning step includes positioning the forward anchor against a portion of the person's head proximally surrounding the breathing orifice.

4. The method of claim 3, further comprising the step of stabilizing the mask attachment device using a compliant sling disposed between the mask attachment device and the person's head and having opposite ends connected to forward and rear portions of the biasing structure.

5. The method of claim 1, wherein the mask attachment device is secured to the person's head without straps utilizing substantially only the occipital anchor, the forward anchor, and the biasing structure.

6. The method of claim 1, further comprising the step of securing the mask attachment device to the person's head using straps that extend from the occipital anchor to the forward anchor.

7. The method of claim 1, further comprising the step of removing expired gas containing carbon dioxide using a vent formed in the mask.

8. The method of claim 1, wherein said positioning step comprises adjusting the positions of the forward and occipital anchors with respect to said biasing structure and each other so as to provide comfortable, secure placement of the breathing mask and mask attachment device on the person's head.

9. In combination, a continuous positive airway pressure (CPAP) system for providing CPAP to a person via a mask to prevent sleep apnea, and a device for holding the mask in place over an orifice in the person's head while the person sleeps, the device comprising an occipital anchor adapted to fit against the head of the person about the occipital lobe of the person;

a forward anchor adapted to fit against a corresponding portion of the person's head at a forward anchoring position selected from the group consisting of a first portion of the person's head proximally surrounding the orifice and a region located from a top portion of the person's head to a forehead portion of the person's head;

a biasing structure connecting the forward anchor and the occipital anchor, the biasing structure adapted to bias the occipital anchor against the head of the person beneath occipital lobe and to bias the forward anchor against the corresponding portion of the person's head so as to attach the device to the person's head, wherein the occipital anchor, the forward anchor and the biasing structure are adapted to be substantially aligned along the axis of symmetry of the person's head; and a mounting member extending from said forward anchor for mounting said apparatus so as to locate the apparatus over said orifice.

10. The combination of claim 9, wherein the mask further comprises a vent sized so that CPAP flushes the system of exhaled gases between breaths.

11. The combination of claim 9, wherein the occipital anchor, forward anchor, biasing structure and mounting member are essentially the only means for holding the breathing mask in place over an orifice in a person's head while the person sleeps.

12. The combination of claim 9, wherein the device further comprises a side strap connecting the occipital anchor with the forward anchor.

13. The combination of claim 9, wherein said biasing member comprises a curved spring having a forward end and a rear end, and wherein said occipital anchor is mounted adjacent said rear end of said spring so as to be movable with respect to said spring so as to permit adjustment of the position of said occipital anchor with respect to said rear end thereof, and said forward anchor is mounted adjacent said forward end of said spring so as to be movable with respect to said spring so as to permit adjustment of the position of said forward anchor with respect to said forward end thereof.

14. The combination of claim 13, further comprising:

a rear scabbard to which said occipital anchor is mounted, said rear scabbard having a slot formed therein for slidably receiving the rear end of said spring; and a forward scabbard to which said forward anchor is mounted, said forward scabbard having a slot formed therein for slidably receiving the forward end of said spring, said mounting structure being connected at a rear end thereof to said forward scabbard.

* * * * *